(12) United States Patent
Yap

(10) Patent No.: US 11,583,503 B2
(45) Date of Patent: Feb. 21, 2023

(54) COMPOSITION FOR PROMOTING WOUND HEALING AND PREPARING METHOD THEREOF

(71) Applicant: BenQ Materials Corporation, Taoyuan (TW)

(72) Inventor: Lie-Sian Yap, Taoyuan (TW)

(73) Assignee: BenQ Materials Corporation, Taoyuan (TW)

( * ) Notice: Subject to any disclaimer, the term of this patent is extended or adjusted under 35 U.S.C. 154(b) by 0 days.

(21) Appl. No.: 17/204,914

(22) Filed: Mar. 17, 2021

(65) Prior Publication Data

US 2022/0105046 A1    Apr. 7, 2022

(30) Foreign Application Priority Data

Oct. 5, 2020  (TW) ................................. 109134458

(51) Int. Cl.
| | | |
|---|---|---|
| *A61K 9/50* | (2006.01) | |
| *A61K 47/26* | (2006.01) | |
| *A61P 17/02* | (2006.01) | |
| *A61K 47/44* | (2017.01) | |
| *A61K 33/04* | (2006.01) | |

(52) U.S. Cl.
CPC .......... *A61K 9/5031* (2013.01); *A61K 9/5089* (2013.01); *A61K 33/04* (2013.01); *A61K 47/26* (2013.01); *A61K 47/44* (2013.01); *A61P 17/02* (2018.01)

(58) Field of Classification Search
CPC .... A61K 9/5031; A61K 9/5089; A61K 33/04; A61K 47/26; A61K 47/44; A61K 9/0014; A61P 17/02
See application file for complete search history.

(56) References Cited

FOREIGN PATENT DOCUMENTS

| CN | 101884623 A | 11/2010 |
|---|---|---|
| CN | 109793919 A | 5/2019 |

OTHER PUBLICATIONS

Hsing-Wen Sung et al., "Development of a Sustained H2s-Releasing Dressing for Wound Healing in Diabetic Ulcers", Institute of Biomedical Engineering, National Tsing Hua University, Jul. 26, 2018.
Jiang Wu et al., "Novel H2S Releasing Nano-fibrous Coating for In Vivo Dermal Wound Regeneration", ACS Applied Materials and Interfaces, Aug. 9, 2016.

*Primary Examiner* — Matthew P Coughlin
*Assistant Examiner* — Thurman Wheeler
(74) *Attorney, Agent, or Firm* — CKC & Partners Co., LLC

(57) ABSTRACT

The present disclosure relates to a composition sustainable-releasing hydrogen sulfide for promoting wound healing and the method for preparing the same. The composition for promoting wound healing comprises a carrier and a plurality of hydrogen sulfide sustained releasing microspheres, wherein the hydrogen sulfide sustained releasing microspheres comprise a hydrophobic polymer, a surfactant and sodium hydrosulfide.

9 Claims, No Drawings

COMPOSITION FOR PROMOTING WOUND HEALING AND PREPARING METHOD THEREOF

CROSS-REFERENCE TO RELATED APPLICATION

This application claims priority to Taiwan Application Serial Number 109134458, filed Oct. 5, 2020, which is herein incorporated by reference in its entirety.

BACKGROUND

Field of Invention

The present disclosure relates to a composition for promoting wound healing and the method for preparing the same. More particularly, the present disclosure relates to a composition sustainable-releasing hydrogen sulfide for promoting wound healing and the method for preparing the same.

Description of Related Art

Angiogenesis is one of the important mechanisms in wound healing. However, because of long-term high blood sugar, the patients with diabetes are prone to vascular disease, such as, vascular sclerosis or blockage, to cause the blood flow at the wound sites poor. The poor blood circulation around the wound sites results in the reduced growth and formation of the blood vessels to delay wound heal. In addition, high blood sugar will also reduce the activity of white blood cells, and the phagocytosis and sterilization functions will become worse. Because the immune function is weak, the wound is continuously infected by bacterial and will inhibit the cell proliferation. This is another factor in delaying the wounds healing of patients with diabetes.

Hydrogen sulfide ($H_2S$) regarded as the third gaseous signaling molecule following the nitric oxide (NO) and carbon monoxide (CO). It has been proved in animal experiments that hydrogen sulfide relates to the relaxation of blood vessels, the inhibition of the proliferation of vascular smooth muscle cells, the induction of vascular smooth muscle cells apoptosis, the promotion of the proliferation of microvascular endothelial cells, anti-inflammatory and antioxidant effects. In the state of the art, it is known that the normal cells can produce low concentration of gaseous hydrogen sulfide in a slow rate. However, the external hydrogen sulfide donor is unable to really mimic the producing rate of hydrogen sulfide in human body.

Sodium hydrosulfide (NaHS) was used as an $H_2S$ donor since NaHS can regenerate $H_2S$ release when contact with water. However, because hydrosulfide ion ($HS^-$) in sodium hydrosulfide reacted with the hydrogen ion ($H^+$) from water to release hydrogen sulfide is very fast, the fast release will induce high concentration of hydrogen sulfide in short time. High concentration of hydrogen sulfide is toxic to cells and will induce adverse effects such as, cell apoptosis or inflammation. Low concentration of hydrogen sulfide will promote the wound healing, but the cytotoxicity induced by the high concentration thereof made the hydrogen sulfide not suitable to be used in medical treatment.

In the state of the art, the wound dressing which can release gaseous hydrogen sulfide has been disclosed, but the effective concentration of hydrogen sulfide released for healing the wound can only last for about 24 hours. It is needed to frequently change the wound dressing in such a circumstance which is not good for wound healing.

Thus, it demands a composition for sustainable-releasing hydrogen sulfide without inducing cytotoxicity but effectively promoting the wound healing.

SUMMARY

The present disclosure is to provide a novel composition for promoting wound healing and the method for preparing the same. The present composition for promoting wound healing can sustainably release hydrogen sulfide, for example, at a releasing concentration in the range of 10 to 50 µM/hr in 48 hours. Thus, the present composition can effectively promote the wound healing without inducing any cytotoxicity.

An aspect of the present disclosure is to provide a composition for promoting wound healing comprising a carrier and a plurality of hydrogen sulfide sustained-releasing microspheres. The hydrogen sulfide sustained-releasing microspheres comprise a hydrophobic polymer, a surfactant and sodium hydrosulfide, wherein the hydrophobic polymer can be, for example, at least one of polycaprolactone (PCL), ethylcellulose and polyglycolide or the combination thereof.

In an embodiment of the present disclosure, the using amount of the carrier is in the range of 300 weight parts to 400 weight parts based on per hundred weight parts of the hydrogen sulfide sustained-releasing microspheres.

In an embodiment of the present disclosure, the particle size of the hydrogen sulfide sustained-releasing microspheres is in the range of 8 microns to 135 microns.

In an embodiment of the present disclosure, the hydrogen sulfide sustained-releasing microspheres comprise 15 to 25 weight parts of the hydrophobic polymer, 0.5 to 1.5 weight parts of the surfactant and 0.5 to 1.5 weight parts of the sodium hydrosulfide.

In an embodiment of the present disclosure, the surfactant can be, for example, at least one of polysorbate 80, polysorbate 20, polysorbate 60, polysorbate 40, sorbitan oleate, glyceryl oleate and laureth-3, or the combination thereof.

In an embodiment of the present disclosure, the weight average molecular weight of the hydrophobic polymer can be in the range of 70,000 to 250,000.

In an embodiment of the present disclosure, the carrier can be, for example, at least one of Vaseline, paraffin gel and beeswax or the combination thereof.

Another aspect of the present disclosure is to provide a method for preparing a composition for promoting wound healing. The method comprises the steps of: dispersing sodium hydrosulfide in a first solvent to form a first solution; adding a hydrophobic polymer into a second solvent to form a second solution; mixing the first solution and the second solution to form a third solution; adding the third solution into an oil containing a surfactant to form a fourth solution; stirring the fourth solution; filtering and drying the fourth solution to form hydrogen sulfide sustained-releasing microspheres; heating and melting a carrier; adding the hydrogen sulfide sustained-releasing microspheres into the melted carrier; and cooling the carrier containing the hydrogen sulfide sustained-releasing microspheres.

In an embodiment of the preparing method of the present disclosure, the using amount of hydrophobic polymer is in the range of 15 to 25 weight parts, the surfactant is in the range of 0.5 to 1.5 weight parts and the sodium hydrosulfide is in the range of 0.5 to 1.5 weight parts.

In an embodiment of the preparing method of the present disclosure, the first solvent and the second solvent can be independently at least one of ethanol, isopropanol, acetone and dimethyl sulfoxide, or the combination thereof.

In an embodiment of the preparing method of the present disclosure, the hydrophobic polymer can be, for example, at least one of polycaprolactone (PCL), ethylcellulose and polyglycolide, or the combination thereof.

In an embodiment of the preparing method of the present disclosure, the weight average molecular weight of the hydrophobic polymer can be in the range of 70,000 to 250,000.

In an embodiment of the preparing method of the present disclosure, the surfactant can be at least one of polysorbate 80, polysorbate 20, polysorbate 60, polysorbate 40, sorbitan oleate, glyceryl oleate and laureth-3, or the combination thereof.

In an embodiment of the manufacturing method of the present disclosure, the oil can be at least one of mineral oil, soybean oil, corn oil and silicon oil or the combination thereof.

In an embodiment of the manufacturing method of the present disclosure, the viscosity of the oil can be in the range of 50 cps to 150 cps.

In an embodiment of the manufacturing method of the present disclosure, the carrier can be, for example, at least one of Vaseline, paraffin gel and beeswax or the combination thereof.

In an embodiment of the manufacturing method of the present disclosure, the ratio of the using amount of the hydrogen sulfide sustained-releasing microspheres to the carrier can be in the range of 1:3 to 1:4.

The above and other aspects of the present disclosure will become better understood with regard to the following detailed description of the preferred but non-limiting embodiment(s). These and other aspects of the present disclosure will become apparent from the following description of the presently preferred embodiments. The detailed description is merely illustrative of the present disclosure and does not limit the scope of the present disclosure, which is defined by the appended claims and equivalents thereof. As would be obvious to one skilled in the art, many variations and modifications of the present disclosure may be affected without departing from the spirit and scope of the novel concepts of the present disclosure.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

It is apparent that departures from specific designs and methods described and shown will suggest themselves to those skilled in the art and may be used without departing from the spirit and scope of the present disclosure. The present disclosure is not restricted to the particular constructions described and illustrated, but should be construed to cohere with all modifications that may fall within the scope of the appended claims.

Unless defined otherwise, all technical and scientific terms used herein have the same meaning as commonly understood by one of ordinary skill in the art to which the present disclosure belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art.

An aspect of the present disclosure is to provide a novel composition for promoting wound healing, which can sustainably release hydrogen sulfide, for example, at a releasing concentration in the range of 10 to 50 μM/hr in 48 hours. The present composition can prevent from releasing high concentration of hydrogen sulfide in a short period of time to induce cytotoxicity and can effectively promote the healing of chronic wound.

In an embodiment of the composition for promoting wound healing of the present disclosure, the composition for promoting wound healing can comprise a carrier and a plurality of hydrogen sulfide sustained-releasing microspheres. In an embodiment of the present disclosure, a ratio of the using amount of the hydrogen sulfide sustained-releasing microspheres and the using amount of the carrier is in the range of 1:3 to 1:4. When the using amount of the carrier is less, the hydrogen sulfide sustained-releasing microspheres cannot be sufficiently encapsulated and hydrogen sulfide may be released during the preparation process. When the using amount of the carrier is exceeded, the amount of the hydrogen sulfide sustained-releasing microspheres will be too less to provide sufficient releasing concentration of hydrogen sulfide to effectively promote the wound healing.

In an embodiment of the present disclosure, the carrier is used to encapsulate the hydrogen sulfide sustained-releasing microspheres to elongate the releasing time of the hydrogen sulfide and to enhance the stability of the composition. The suitable carrier can be, but not limited to, for example, at least one of Vaseline, paraffin gel and beeswax, or the combination thereof.

In an embodiment of the present disclosure, the hydrogen sulfide sustained-releasing microspheres can comprise a hydrophobic polymer, a surfactant and a sodium hydrosulfide. In an embodiment of the hydrogen sulfide sustained-releasing microspheres of the present disclosure, the hydrogen sulfide sustained-releasing microspheres can comprise 15 to 25 weight parts of the hydrophobic polymer, 0.5 to 1.5 weight parts of the surfactant and 0.5 to 1.5 weight parts of the sodium hydrosulfide. If the adding amount of the sodium hydrosulfide is exceeded, the released concentration of the hydrogen sulfide gas is high to cause cytotoxicity. If the adding amount of the sodium hydrosulfide is less, the released concentration of the hydrogen sulfide gas is low to insufficiently promote the wound healing.

The particle size of the hydrogen sulfide sustained-releasing microspheres will affect the releasing rate of the hydrogen sulfide. In an embodiment of the present disclosure, the suitable particle size of the hydrogen sulfide sustained-releasing microspheres can be in the range of 8 microns to 135 microns.

The hydrophobic polymer is used to encapsulate the sodium hydrosulfide for avoiding the sodium hydrosulfide from contacting moisture to release hydrogen sulfide gas too quickly, so the releasing rate of the hydrogen sulfide can be slowed down and controlled. In an embodiment of the present disclosure, the weight average molecular weight of the hydrophobic polymer can be in the range of 70,000 to 250,000. The suitable hydrophobic polymer can be at least one of polycaprolactone (PCL), ethylcellulose and polyglycolide, or the combination thereof.

The hydrogen sulfide sustained-releasing microspheres can be prepared by emulsification. The particle sizes, shapes and the surface area of the hydrogen sulfide sustained-releasing microspheres can be adjusted by the ratio of the surfactant used with in order to adjust the releasing rate of the hydrogen sulfide. In an embodiment of the present disclosure, the surfactant can be at least one of polysorbate 80, polysorbate 20, polysorbate 60, polysorbate 40, sorbitan oleate, glyceryl oleate and laureth-3, or the combination thereof. When the using amount of the surfactant is exceeded, the particle size of the hydrogen sulfide sustained-releasing microspheres might be too small, the hydrogen sulfide sustained-releasing microspheres might have irregular shape or rough surface to cause the releasing rate of the hydrogen sulfide too fast and result in a high releasing concentration thereof. When the using amount of the surfactant is less, the particle size of the hydrogen sulfide sustained-releasing microspheres might be too large and affect the releasing rate of the hydrogen sulfide.

The present composition for promoting wound healing is prepared by encapsulating the sodium hydrosulfide by a hydrophobic polymer to form a hydrogen sulfide sustained-releasing microspheres and encapsulating the hydrogen sulfide sustained-releasing microspheres by a carrier. Accordingly, the cytotoxicity caused by high concentration of the hydrogen sulfide can be prevented, the releasing time of the hydrogen sulfide can be extended, the stability of the composition can be enhanced, and the users' convenience can be increased.

Another aspect of the present disclosure is to provide a method for preparing the composition for promoting wound healing. The present method can comprise but not limited to the following steps.

Firstly, sodium hydrosulfide is dispersed into a first solvent to form a first solution, a hydrophobic polymer is added into a second solvent to form a second solution, and then the first solution and the second solution are mixed to form a third solution. In an embodiment of the preparation method of the present disclosure, when the hydrophobic polymer is added into the second solvent for preparing the second solution, it optionally further comprises a step of heating for melting the hydrophobic polymer, the heating temperature can be varied with the hydrophobic polymer used. In a preferred embodiment of the preparation method of the present disclosure, the heating temperature can be in the range of 40° C. to 60° C.

In an embodiment of the preparation method of the present disclosure, the using amount of the sodium hydrosulfide can be in the range of 0.5 to 1.5 weight parts and the using amount of the hydrophobic polymer can be in the range of 15 to 25 weight parts.

The first solvent and the second solvent can be the same or different. The suitable first solvent and the suitable second solvent can be independently at least one of ethanol, isopropanol, acetone and dimethyl sulfoxide, or the combination thereof. In an embodiment of the preparation method of the present disclosure, the first solvent can be ethanol and the second solvent can be acetone.

After the third solution is thoroughly stirred, the third solution is added into an oil containing a surfactant to form a fourth solution, and then the fourth solution is stirred. In an embodiment of the preparation method of the present disclosure, the using amount of the surfactant can be in the range of 0.5 to 1.5 weight parts.

The suitable surfactant used in the present method can be but not limited to at least one of polysorbate 80, polysorbate 20, polysorbate 60, polysorbate 40, sorbitan oleate, glyceryl oleate and laureth-3, or the combination thereof.

The particle size of the hydrogen sulfide sustained-releasing microspheres can be adjusted by selecting the oil used for and the stirring speed of the fourth solution. In an embodiment of the preparation method of the present disclosure, the viscosity of the oil can be in the range of 50 cps to 150 cps. The suitable oil can be but not limited to, for example, mineral oil, soybean oil, corn oil and silicon oil, or the combination thereof.

After the fourth solution is stirred, the fourth solution is filtered and dried to form the hydrogen sulfide sustained-releasing microspheres. In an embodiment of the preparation method of the present disclosure, the particle size of the hydrogen sulfide sustained-releasing microspheres can be in the range of 8 microns to 135 microns.

Next, the hydrogen sulfide sustained-releasing microspheres are added in to a melted carrier. The suitable carrier can be but not limited to, for example, at least one of Vaseline, paraffin gel and beeswax, or the combination thereof. In an embodiment of the preparation method of the present disclosure, the ratio of the using amount of the hydrogen sulfide sustained-releasing microspheres to the using amount of the carrier can be in the range of 1:3 to 1:4.

Then, the carrier comprising hydrogen sulfide sustained-releasing microspheres is cooled down to prepare a composition for promoting wound healing.

The present disclosure will be described below with reference to Examples to describe the present disclosure in detail but the present disclosure is not limited to the description thereof.

EXAMPLE

Example 1

0.23 g of sodium hydrosulfide was dispersed in 1.5 ml of ethanol and stirred for 3 hours at room temperature to form a first solution. 2 g of polycaprolactone (the weight average molecular weight was about 80,000) was dissolved in 8.5 ml of acetone, and then heated and stirred at 50° C. for 10 minutes to form a second solution. Then, the first solution and the second solution were mixed and stirred at room temperature for 15 minutes to form a third solution. The third solution was dropped into 100 ml of mineral oil (Kaydol white mineral oil, commercially obtained from Sonneborn, US) containing 1 ml of sorbitan monooleate (Span80) as surfactant, stirred for 30 minutes at room temperature and filtered the solution by vacuumed suction to obtain filter cake. The filter cake was washed by N-heptane and dried in oven for 2 hours to obtain the hydrogen sulfide sustained-releasing microspheres. And then, 3.5 g of Vaseline was heated to 60° C. for liquefying and cooled down to 40° C. 1 g of the resulting microspheres was added into the Vaseline and stirred for 10 minutes. The resulting Vaseline mixture was kept stirring until cooling down to room temperature and being viscous, and then, the mixture was dried in oven to obtain a composition for promoting wound healing.

Example 2

The steps and materials used in Example 2 are the same as those of Example 1, except that 0.3 g of sodium hydrosulfide was instead of 0.23 g of sodium hydrosulfide, 2 ml of ethanol was instead of 1.5 ml of ethanol and 8 ml of acetone was instead of 8.5 ml of acetone.

Comparative Example 1

The steps and materials used in Comparative example 1 are the same as those of Example 1, except that 2.5 g of Vaseline was instead of 3.5 g of Vaseline.

Comparative Example 2

The steps and materials used in Comparative example 2 are the same as those of Example 1, except that 5 g of Vaseline was instead of 3.5 g of Vaseline.

The composition for promoting wound healing obtained from the Examples 1 and 2 and Comparative examples 1 and 2 was tested in accordance with the following method.

Determination of the Releasing Rate of the Hydrogen Sulfide

The releasing concentration of the hydrogen sulfide was determined by the Methylene Blue method. The Methylene Blue method is a known method for determining the concentration of sulfide in aqueous solution containing the same in a low level.

Firstly, standard sample with known concentration were prepared for building the calibration curve. The preparation of the calibration curve was as follows: preparing 0.04 mg/mL sodium hydrosulfide in 500 μL phosphate buffer (pH=7.4) and diluting in series of standard samples with different concentration and preparing phosphate buffer without sodium hydrosulfide. 100 μL of each of the standard sample was mixed with 100 μL of 1.0 wt % zinc acetate aqueous solution and then, added 20 μL of 20 mM N,N-dimethyl-p-phenylenediamine sulfate in 7.2 N hydrogen chloride aqueous solution and 20 μL of 30 mM $FeCl_3$ in 1.2 N hydrogen chloride aqueous solution to react 20 minutes at 32° C. The $FeCl_3$ was acted as oxidant to catalyze the N,N-dimethyl-p-phenylenediamine sulfate to react with hydrogen sulfide, the product of sodium hydrosulfide dissolved in water, to produce methylene blue. The absorbance of each standard sample at wavelength of 670 nm was determined to build the calibration curve and calculate the concentration of the hydrogen sulfide.

Next, each of 10 mg of the compositions for promoting wound healing obtained from Examples 1 and 2 and Comparative examples 1 and 2 was added into 1500 μL of phosphate buffer and allowed to stand at 32° C. 100 μL of phosphate buffer containing hydrogen sulfide was taken out every hour and heated at 75° C. for 2 minutes to release the remained hydrogen sulfide. The phosphate buffer was then added 100 μL of 1.0 wt % zinc acetate aqueous solution, 20 μL of 20 mM N,N-dimethyl-p-phenylenediamine sulfate in 7.2N hydrochloric acid, and 20 μL of 30 mM $FeCl_3$ in 1.2N hydrogen chloride aqueous solution for reacting 20 minutes at 32° C. The resulting solution was detected the methylene blue absorbance at wavelength of 670 nm to determine the average released amount of the sodium hydrosulfide of the compositions obtained from Examples and Comparative examples in every hour during the periods of 0 to 24 hours and 24 to 48 hours. The test results are shown in the following Table 1.

The determine method of the amount of sodium hydrosulfide

Each of 10 mg of the compositions for promoting wound healing obtained from Examples 1 and 2 and Comparative examples 1 and 2 was added into 1500 μL of phosphate buffer and were heated at 75° C. for 2 minutes. After hydrogen sulfide was released, 100 μL of phosphate buffer containing hydrogen sulfide was taken out and added 100 μL of 1.0 wt % zinc acetate aqueous solution, 20 μL of 20 mM N,N-dimethyl-p-phenylenediamine sulfate in 7.2 N hydrogen chloride aqueous solution, and 20 μL of 30 mM $FeCl3$ in 1.2 N hydrogen chloride aqueous solution for reacting 20 minutes at 32° C. The resulting solution was detected the methylene blue absorbance at wavelength of 670 nm to determine the total amount of the sodium hydrosulfide in the compositions obtained from Examples and Comparative examples. The test results are shown in the following Table 1.

The test results are shown in Table 1.

TABLE 1

| | The test results of Examples 1 to 2 and Comparative examples 1 to 2 | | |
|---|---|---|---|
| | The average releasing concentration of hydrogen sulfide in 0 to 24 hours (μM/hr) | The average releasing concentration of hydrogen sulfide in 24 to 48 hours (μM/hr) | The amount of sodium hydrosulfide (μM/10 mg) |
| Example 1 | 18.27 | 10.87 | 1373.7 |
| Example 2 | 18.3 | 14.5 | 1527.6 |
| Comparative example 1 | 23.55 | 4.15 | 840.54 |
| Comparative example 2 | 12.72 | 5.90 | 649.80 |

The composition for promoting wound healing obtained from Examples 1 and 2 effectively sustained-released the hydrogen sulfide gas in 48 hours without exceeding the safety concentration. The composition for promoting wound healing obtained from Comparative examples 1 and 2 released and maintained at the concentration higher than 10 μM/hr only for 24 hours and less than 10 μM/hr after 24 hours and thus, the wound healing cannot be effective promoted.

Animal Experiment Result

Animal Experiment were performed using three BKS.Cg-Leprdb/Leprdb/JNarl (leptin receptor-deficient diabetes, db/db, 13 weeks, (commercially obtained from National Laboratory Animal Center, Taipei, Taiwan) mice with high plasma glucose levels of >600 mg/dL, which is a well-established diabetic animal model. Mice were anaesthetized with inhaled isoflurane. Three 5-mm-diameter full-thickness skin wounds (volume, approximately 50 μL) were made symmetrically to the dorsal skin of a single mouse with a biopsy punch and treated with the following different treatments. The wounds of Control group 1 were applied with normal saline and covered with breathable dressing (Tegaderm™, 3M). The wounds of Control 2 were applied 20 mg of Vaseline and covered with breathable dressing. The wounds of Control group 3 were applied 20 mg of the composition obtained from Example 2 and covered with breathable dressing. Test mice were housed individually to avoid disturbing wound healing. The wounds treated with the same manner were in different wound sites on each mouse in order to decrease the factors of wound location to the wound heal. Wound-closure rates were measured by tracing the wound area every other day.

After the dressings were changed and the wound bed was washed with phosphate buffer solution every other day, the wound area change was digitally photographed by Image software. The original wound area as set as 100 and the wound-closure rates was expressed as the percentage of the wound area that had healed. The change of the wound area as shown in Table 2.

TABLE 2 the wound healing of Control groups

| Time (Days) | Control group 1 | Control group 2 | Control group 3 |
|---|---|---|---|
| 0 | 100 | 100 | 100 |
| 2 | 116.9 ± 11.7 | 117 ± 9 | 106 ± 7.8 |
| 4 | 106 ± 21.7 | 101.9 ± 15.4 | 100.9 ± 7.6 |
| 8 | 48.9 ± 7 | 48 ± 4 | 41.8 ± 14.5 |
| 10 | 22.7 ± 13 | 17.9 ± 16 | 0 |

As shown in Table 2, as time being, the wounds in each control group were gradually contracted, but on the tenth day, the wound sites of the mice applied with normal saline solution and Vaseline is still significant. The wound sites treated with the composition obtained from Example 2 were completely healed. Accordingly, the present composition for promoting wound healing can effectively promote the wound healing.

Although particular embodiments have been shown and described, it should be understood that the above discussion is not intended to limit the present disclosure to these embodiments. Persons skilled in the art will understand that various changes and modifications may be made without departing from the scope of the present disclosure as literally and equivalently covered by the following claims.

What is claimed is:

1. A method for preparing a composition for promoting wound healing comprising the steps of:
   dispersing sodium hydrosulfide into a first solvent to form a first solution;
   adding a hydrophobic polymer into a second solvent to form a second solution,
   wherein the hydrophobic polymer is selected from the group consisting of polycaprolactone (PCL), ethylcellulose, polyglycolide and combinations thereof, and a weight ratio of the using amount of the hydrophobic polymer to the using amount of the sodium hydrosulfide is 15-25:0.5-1.5;
   mixing the first solution and the second solution to form a third solution;
   adding an oil containing a surfactant into the third solution to form a fourth solution;
   stirring the fourth solution;
   filtrating and drying the fourth solution to form the plurality of hydrogen sulfide sustained-releasing microspheres;
   heating and melting a carrier;
   adding the plurality of hydrogen sulfide sustained-releasing microspheres into the melting carrier; and
   cooling the carrier containing the plurality of hydrogen sulfide sustained-releasing microspheres.

2. The method as claimed in claim 1, wherein a weight ratio of the using amount of the hydrophobic polymer to the using amount of the surfactant is to the using amount of the sodium hydrosulfide is 15-25:0.5-1.5:0.5-1.

3. The method as claimed in claim 1, wherein the first solvent and the second solvent is selected from the group consisting of ethanol, isopropanol, acetone, dimethyl sulfoxide and combinations thereof.

4. The method as claimed in claim 1, wherein the weight average molecular weight of the hydrophilic polymer is in the range of 70,000 Da to 250,000 Da.

5. The method as claimed in claim 1, wherein the surfactant is selected from the group consisting of polysorbate 80, polysorbate 20, polysorbate 60, polysorbate 40, sorbitan oleate, glyceryl oleate, laureth 3 and combinations thereof.

6. The method as claimed in claim 1, wherein the oil is selected from the group consisting of mineral oil, soybean oil, corn oil, silicone oil and combinations thereof.

7. The method as claimed in claim 1, wherein the viscosity of the oil is in the range of 50 cps to 150 cps.

8. The method as claimed in claim 1, wherein the carrier is selected from the group consisting of petroleum jelly, paraffin gel and beeswax and combinations thereof.

9. The method as claimed in claim 1, wherein ratio of the using amount of each of the plurality of the hydrogen sulfide sustained-releasing microspheres to the using amount of the carrier is in the range of 1:3 to 1:4.

* * * * *